United States Patent [19]

Matsuura et al.

[11] 4,041,437
[45] Aug. 9, 1977

[54] HUMIDITY SENSOR

[75] Inventors: Mikio Matsuura; Nobuji Nishi; Masatsugu Yamaguchi, all of Hirakata; Michio Matsuoka, Ibaragi; Takeshi Masuyama, Takatsuki, all of Japan

[73] Assignee: Matsushita Electric Industrial Co., Ltd., Japan

[21] Appl. No.: 644,414

[22] Filed: Dec. 24, 1975

[30] Foreign Application Priority Data

Dec. 27, 1974 Japan .................................. 50-2791
Jan. 20, 1975 Japan .................................. 50-8896
Jan. 20, 1975 Japan .................................. 50-8897
Jan. 20, 1975 Japan .................................. 50-8898

[51] Int. Cl.² .......................................... H01C 13/00
[52] U.S. Cl. ........................................ 338/35; 73/29; 73/73; 73/336.5; 23/253 R; 252/194; 252/408
[58] Field of Search ............... 252/408, 194, 474, 476, 252/518; 73/19, 29, 73, 335, 336.5; 23/253 R; 338/34, 35

[56] References Cited

U.S. PATENT DOCUMENTS

| 3,200,167 | 8/1965 | Reich | 252/476 |
| 3,671,913 | 6/1972 | Mamiya et al. | 73/29 |
| 3,715,702 | 2/1973 | Nicholas | 73/335 |
| 3,870,655 | 3/1975 | Nanba | 252/476 |

OTHER PUBLICATIONS

Chemical Abstracts, vol. 70, (1969) No. 61495g.
Shibata et al., Bulletin of the Chem. Soc. of Japan, vol. 42, 1969, pp. 871-874.

Primary Examiner—Benjamin R. Padgett
Assistant Examiner—Irwin Gluck
Attorney, Agent, or Firm—Wenderoth, Lind & Ponack

[57] ABSTRACT

This invention provides a humidity sensor having a negative coefficient of resistivity for relative humidity, which comprises 99.99 to 10 mole percent of iron oxide ($Fe_2O_3$) and 0.01 to 90 mole percent of at least one member selected from alkali metal oxides, which are lithium oxide ($Li_2O$), sodium oxide ($Na_2O$), potassium oxide ($K_2O$) and cesium oxide ($Cs_2O$). The amount of the alkali metal oxide in the sensor is preferably 0.01 to 25 mole percent. This sensor is advantageous because it can accurately detect the changes in humidity and it has a long, stable life.

11 Claims, 7 Drawing Figures

HUMIDITY SENSOR

This invention relates to a humidity sensor, and more particularly to such humidity sensors which respond to changes in atmospheric water content by changes in electrical resistivity.

Various humidity sensors have heretofore been known which detect changes in relative humidity in an atmosphere in terms of changes in electrical resistivity (hereinafter referred to merely as "resistivity"). These humidity sensors are made of a film such as lithium chloride (LiCl) infiltrated into or onto a porous matrix body, resin having a metal such as gold (Au) or silver (Ag) dispersed therein, an anthracene single crystal having a surface oxidized by ozone, a P- or N-type silicon (Si) single crystal, a hydrophilic organic polymer film having carbon dispersed therein, metals having an oxidized surface such as anodically oxidized porous aluminum, and metal oxide systems such as magnetite ($Fe_3O_4$), $Si-Na_2O-V_2O_5$ glass, selenium oxide ($SeO_2$), stannic oxide-antimony oxide ($SnO_2-Sb_2O_3$), manganese oxide-titanium oxide ($Mn_3O_4-TiO_2$), barium titanate ($BaTiO_3$), lithium ferrite ($LiFe_2O_4$), and hematite ($Fe_2O_3$). However, these humidity sensors have not come into extensive use for humidity measurement and control devices, because they have many defects for practical use.

As for the humidity sensors to be used for these types of devices, it is required that the resistivity of the sensors vary greatly with the change of humidity over the entire range of the relative humidity, or at a special point or range of the relative humidity to be used. Representative examples of the humidity sensors already known are a sensor prepared by coating a high molecular weight substance serving as an insulator with a thin film of a hygroscopic electrolytic salt such as lithium chloride, for example, and a sensor prepared by impregnating a porous synthetic resin with a hygroscopic electrolytic salt such as lithium chloride (hereinafter referred to merely as a lithium chloride humidity sensor). In the case of these humidity sensors, the salt becomes dry wet in corresponding relationship to the changes in the relative humidity of the atmosphere, and by virtue of the flow of current, the changes in the amount of moisture taken up are detected in terms of the changes in the resistivity of the humidity sensor. However, because of its nature properties, the above-mentioned hydroscopic electrolytic salt dissolves in a highly humid atmosphere upon absorption of a large amount of moisture and is no longer usable as a resistive layer (film), so that the humidity sensors including a salt such as lithium chloride have a great limitation in that they can be used only under restricted humidity conditions. Further, they have a defect in that the resistivity varies greatly with the change in temperature. Another defect of the lithium chloride humidity sensor is its unstable resistivity-humidity characteristics, when used at an ambient temperature of above 35° C. The change of resistivity after 6 months at 35° C, for example, becomes more than 10% R.H. (relative humidity) in the read-out humidity change caused by resistivity change. Another defect of this type of humidity sensor is its slow response of resistivity against humidity change in the atmosphere. For example, for 40 to 80% R.H. change of relative humidity at 20° C, 5 to 40 minutes and 10 to 80 minutes are required to cause a complete change in resistivity for adsorption and desorption processes, respectively. Another defect of the lithium chloride humidity sensor is its high resistivity in the lower humidity region, i.e., less than 40%. R.H. Because of its rather short stability of resistivity-humidity characteristics, e.g., up to a year, the practically usable humidity region of this humidity sensor is limited to between about 40 and 90% R.H., even at near room temperature (under 35° C).

As for another example of the humidity sensor where magnetite ($Fe_3O_4$) is used as a resistive material, a colloidal liquid containing particles of magnetite with a particle size of about 100A, for example, is prepared, and the liquid is then applied or sprayed onto an insulating substrate to form a coating, since magnetite loses its humidity-resistance characteristics (R-H characteristics) when fired at a temperature more than 150° C. The obtained coating of the humidity sensor, however, is poor in mechanical strength. It is easily removed mechanically or by thermal shock and becomes unstable once peeling takes place. This humidity sensor is used in a humidity range of 30 to 95% R.H. and the resistivity changes negatively from $10^8$ ohms to $10^4$ ohms with an increase of moisture in atmosphere. However, these R-H characteristics are strongly affected by the process conditions such as washing out alkali used in a process of co-precipitation, by thickness of the magnetite film and by heat-treating condition, and this causes poor reproducibility and yield. Another defect of the magnetite humidity sensor is its large hysteresis, which means resistivity change between ascending humidity and descending humidity, especially in a moist atmosphere, i.e., near 90% R.H. That is, the time constant of desorption of water is much larger than that of adsorption. Moreover, the magnetite humidity sensor has the defects of poor stability in gas atmosphere and strong temperature dependence of R-H characteristics. Because the R-H characteristics of the magnetite humidity sensor depend on the contact between small particles of magnetite ($Fe_3O_4$), the resistivity increases when a part of the surface of the magnetite is oxidized to γ-Hematite (γ-$Fe_2O_3$). The oxidation reaction of the magnetite sensor is determined by the temperature of practical use. It occurs even at lower temperature and is promoted by increasing temperature. Stability and the maximum temperature for practical use are determined by the degree of oxidation of magnetite to γ-hematite, and this humidity sensor is not used at a high temperature such as 100° C and is not suitable for uses requiring high stability. Further, when relative humidity decreases below 30% RH, the resistivity of the sensor is excessively increased, e.g., to higher than $10^8$ ohm.

As humidity sensors for the medium humidity region, lithium chloride, magnetite, a glassy $Si-Na_2O-V_2O_5$ film, a surface oxidized n- or p-type silicone (Si) and an evaporated germanium (Ge) are also well known. All the humidity sensors mentioned above have many defects as have the former examples, and there is no sensor in wide practical use.

Another humidity sensor is also known which is made by reacting an organic terpene compound with ozone gas and adsorbing the resulting fuming substance on a single crystal of oxidized anthracene. The thus obtained product is used as a humidity sensor as is. However, as this sensor has an inherently very high resistivity, it is used only for special devices which incorporate some other electrical elements having electrical characteristics corresponding to the high resistivity of the sensor, and further, its accuracy is not satisfactory.

Another humidity sensor is also known which is made by dispersing of terpenized gold (Au) into an organic high molecular substance. The thus prepared product is used as a humidity sensor for the low humidity region. However, this is not used widely because of its many defects such as irregularity of particle size of gold, expensive cost of raw material, poor stability in practical use, low yield and small change of resistivity.

As described hereinbefore, almost of the conventional humidity sensors are used in the humidity region between 30 to 90% R.H. and their structures are limited to the form of film. In the prior art, there are a few sensors used for the low humidity region, i.e., less than 30% R.H. For surface type humidity sensors, the improvement of R-H characteristics is quite limited because lowering of resistivity is possible only by increasing surface area and electrode length or distance. Moreover, the temperature for practical use of the surface type humidity sensors is limited to below 50° C at most. Further, as described above, the conventional surface type humidity sensor exhibits poor stability during practical use and accelerated life tests such as the humidity cycle test, temperature cycle or shock test, mechanical shock test, humidity test at a constant temperature, dust test and gas test. In order to increase stability of the sensor film, it has been attempted to provide a humidity sensor by heat-treatment of metal oxide at a high temperature, e.g., more than 1000° C. Although the thus provided sensor has a linear negative response in resistivity with increasing atmospheric humidity, it has a high resistivity and exhibits a resistivity change of merely $10^2$ to $10^3$ in order at most against 20 to 90% R.H. humidity change, and further it has large temperature dependence of R-H characteristics for the temperature range of from 0° to 100° C. Moreover, the manufacturing process for the conventional humidity sensor is complex and comprises the steps of first sintering at high temperature, crushing and firing in film at a temperature lower than that of the first sintering, and it results in poor reproducibility, yield and stability.

As described hereinbefore, in the prior art there is no humidity sensor which can be used over the entire humidity region of from 0 to 100% R.H., and in the temperature region of from 0° to 100° C, with high stability, high mechanical strength, high yield, low cost and ease of manufacturing on an industrial scale. On the other hand, a requirement has recently developed that a humidity sensor be used not only at near room temperature but also even at high temperature, e.g., at 100° C, for example, to detect the humidity in certain kinds of electric driers and humidity generators.

Therefore, an object of this invention is to provide a novel and improved humidity sensor which is capable of accurately detecting the changes in humidity in terms of the changes in resistivity over the entire range of the relative humidity.

Another object of this invention is to provide a humidity sensor which is capable of accurately detecting the changes in humidity in terms of the changes in resistivity in a special range of relative humidity, for example, at less than 50% R.H., at around 50% R.H. or 90% R.H.

A further object of this invention is to provide a humidity sensor which is free of deterioration in respect of the humidity-resistivity characteristics thereof even when used repeatedly at a very high ambient temperature of up to 100° C, or which is practically used as an electrical element to detect dryness at elevated temperature, e.g., even at 150° C.

A further object of this invention is to provide a humidity sensor which will undergo hardly any change in resistivity when subjected to varying temperatures, and which has a resistivity in a practical range and therefore does not require the use of a special device including some other special electrical elements.

A further object of this invention is to provide a humidity sensor comprising a porous sintered body having the humidity-resistivity characteristics thereof at the surface of small particles or grains in that sintered body and having excellent mechanical strength.

These and other objects of this invention are achieved by providing a humidity sensor according to the present invention, that is a humidity sensor having a negative coefficient of resistivity for relative humidity which comprises 99.99 to 10 mole percent of iron oxide ($Fe_2O_3$) and 0.01 to 90 mole percent of at least one member selected from alkali metal oxides, which are lithium oxide ($Li_2O$), sodium oxide ($Na_2O$), potassium oxide ($K_2O$) and cesium oxide ($Cs_2O$).

These objects and features of the present invention will become more apparent from consideration of the following description together with accompanying the drawings, in which.

The inventors have found that by providing the humidity sensor of this invention as described above, it is possible to accurately detect relative humidity since the resistivity thereof varies abruptly in the exponentially functional relationship to the change in humidity over the entire relative humidity range, or at a special relative humidity range, i.e., the lower, middle or high relative humidity range. It is also found that even under repeated use in a very humid atmosphere, practical relative humidity and at elevated ambient temperature of up to 150° C, the sensor's humidity-resistivity characteristics are not impaired, and that the changes in temperature do not produce any substantial change in resistivity of the sensor. The sensor of the invention can be used for humidity measurement not only in the usual state but also in the dry and wet state and it can be advantageously used for a control device since the changes in resistivity over the range of relative humidity of 0 to 100% are in a relatively low range of about $10^7$ ohm-cm to $10^9$ ohm-cm. Further, the sensor of the invention exhibits humidity-resistivity characteristics at the surface of small particles or grains in a porous sintered body, and it has excellent mechanical strength.

For the humidity sensor of this invention, the amounts of the iron oxide ($Fe_2O_3$) and at least one member selected from alkali metal oxides, which are lithium oxide ($Li_2O$), sodium oxide ($Na_2O$), potassium oxide ($K_2O$) and cesium oxide ($Cs_2O$), are essentially critical for achieving the effects described above. In the first place, it is required that the amount of alkali metal oxides be 0.01 to 90 mole percent. When the amount is less than 0.01 mole percent, exponentially functional relationship is not obtained between the relative humidity and the resistivity even at very high relative humidity with porous sintered body and the resistivity becomes much higher than $10^7$ ohm-cm. When the amount is more than 90 mole percent, the resistivity is much decreased and exponentially functional relation is not obtained with stable humidity-resistivity characteristics. According to the experiments, the preferred amount of the alkali metal oxide is 0.01 to 25 mole percent. The alkali metal oxides may be at least one member selected from lithium oxide ($Li_2O$), sodium oxide ($Na_2O$), potassium oxide ($K_2O$) and cesium oxide ($Cs_2O$), and among these alkali oxides potassium oxide is particularly preferable.

In order to obtain high sensitivity and abrupt change of resistivity in a high relative humidity, e.g., around 90% R.H., it is essential according to the experiments that at least one member selected from alkali metal oxides, particularly, potassium oxide ($K_2O$), be contained in amount of 0.01 to less than 2.0 mole percent. When the amount is less than 0.01 mole percent or more than 2.0 mole percent, there is provided no exponentially functional relationship nor any other regular relationship between the relative humidity and the resistivity in high relative humidity, and there are no sensor characteristics. Further, it is essential that at least one member selected from alkali metal oxides, particularly potassium oxide ($K_2O$), be contained in an amount of more than 2.0 to less than 4.0 mole percent, in order to obtain high sensitivity and steep linear inclination in the exponentially functional humidity-resistivity relationship over the whole range of relative humidity. The amount of lower than 2.0 mole percent and more than 4.0 mole percent provides no exponentially functional relationship between the relative humidity and the resistivity. Moreover, it is essential that at least one member selected from alkali metal oxides, particularly potassium oxide ($K_2O$) be contained in an amount of more than 4.0 to less than 25 mole percent, in order to obtain high sensitivity and abrupt change in resistivity in low relative humidity, e.g., less than 50% R.H. in case of potassium oxide ($K_2O$), for example. In case of more than 25 mole percent, the resistivity is decreased according to an exponentially functional relation with the relative humidity, but it also varies with the changes in temperature in low resistivity. Further, it results in poor mechanical strength and poor sintered body.

The humidity sensor according to this invention is made by the following method. The starting materials iron oxide and at least one member selected from alkali oxides are weighed and well mixed in a wet mill so as to produce a homogeneous mixture by per se well known ceramic technique. The mixture is dried and granulated by passing through a 500 $\mu$ mesh sieve with organic binder aqueous solution, and then is pressed in a mold under a pressure from 50 to 500 kg/cm$^2$ into a disc of 17.5 mm in diameter and 1.4 mm in thickness. The pressed body is then sintered in air at a temperature from 800° to 1400° C for 0.5 to 50 hours, and then is cooled in a furnace to room temperature (about 20° C). Then, silver electrodes are applied on both surfaces of the sintered body by firing at about 350° to 900° C. A firing temperature lower than 350° C is undesirable to realize sufficient mechanical strength of the humidity sensor, and the firing temperature higher than 900° C is also undesirable because silver electrodes melt and do not act as electrodes.

Figure 5:
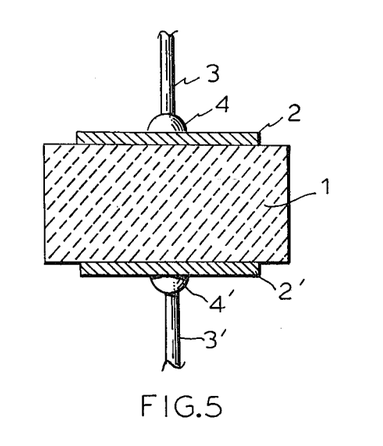
FIG. 5 is a sectional view of an embodiment of the humidity sensor of the invention.

FIG. 5 is a sectional view of the humidity sensor of the invention made as described above, in which silver electrodes 2 and 2' are applied to the both surfaces of a sintered body 1 and lead wires 3 and 3' are attached to the electrodes 2 and 2' by solder ohmic contacts 4 and 4', respectively. However, as described hereinafter, it is also possible to provide a humidity sensor according to the invention in a different form such as a film made by crushing the sintered body provided as described above to form a paste and applying and firing the paste to a base.

The humidity-resistivity characteristics of the resultant sensors of the sintered body are measured in a constant humidity and temperature chamber at a temperature of from 0° to 100° C and in a humidity range of from 0 to 100% R.H. The electrical characteristics of the thus obtained humidity sensor of this invention will become more apparent from the examples described below. The following examples are meant to illustrate preferred embodiments of this invention, but are not meant to limit the scope thereof.

EXAMPLE 1

Figure 1:
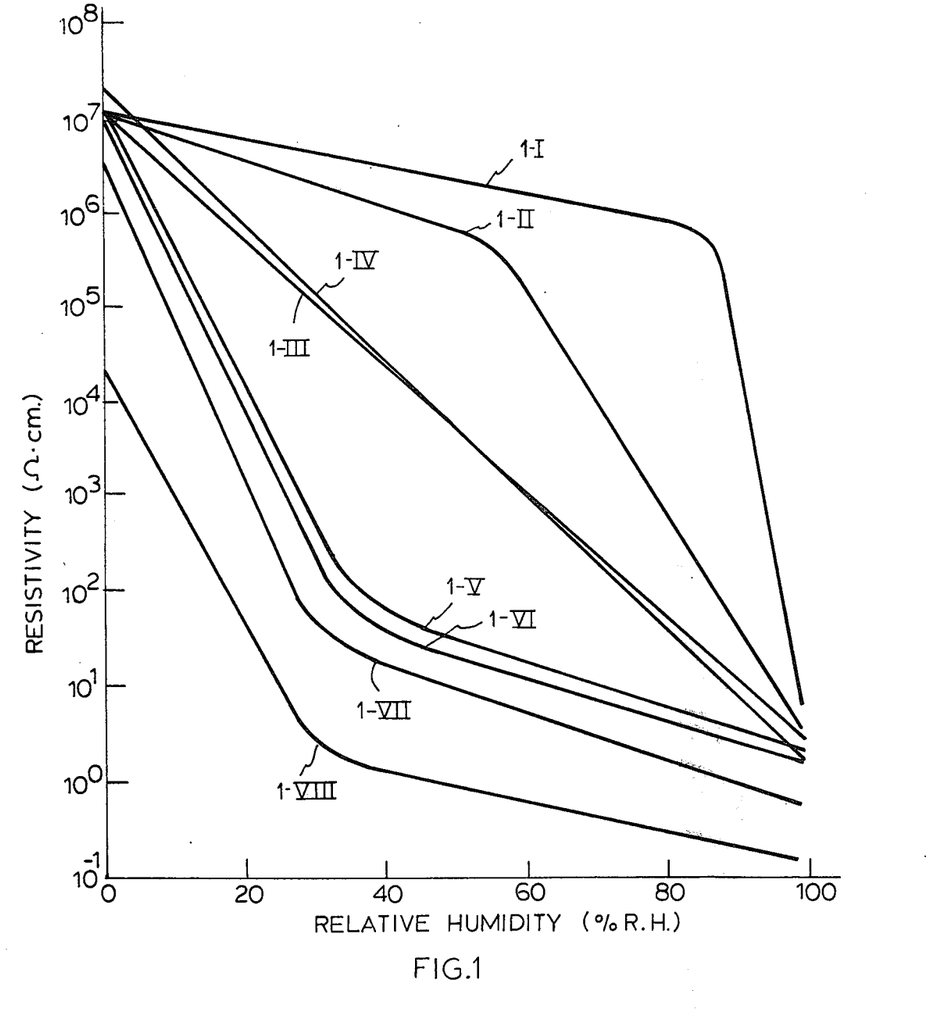
FIGS. 1 to 4 are graphs representing relations of relative humidity vs. resistivity of the humidity sensors according to the invention.

A starting composition as listed in Table 1 was sintered at 1300° C for 2 hours and the humidity sensors were made by the method as described above. The samples were then placed in a constant humidity chamber kept at 80° C, and the change in resistivity corresponding to the humidity changes were measured by constant voltage of 10 volts having a standard frequency of 100Hz. The results of the measured humidity-resistivity characteristics are shown in FIG. 1. From the humidity-resistivity curves shown in FIG. 1, it is apparent that the operable minimum and the maximum amount of potassium oxide in the humidity sensor (resistor) of this invention is 0.01 and 90 mole percent, respectively. For the resistors containing 0.01 to 90 mole percent of potassium oxide prepared from the starting composition of Nos. 1-I to 1-VIII in accordance with this invention, the resistivity varies in exponentially functional relationship to the changes in relative humidity at any range of humidity, e.g., low humidity (Nos. 1-V to 1-VIII), over the whole range (Nos. 1-III and 1-IV) or at high humidity (Nos. 1-I and 1-II).

Even when the humidity-resistivity characteristics were measured with the protection of a guard ring to prevent leak-current through the side surface of the sintered body, quite the same results were obtained. Accordingly, it is clear that the humidity-resistivity characteristics of the sensor of this invention is attributed to the bulk of the sintered body itself. It is also easy to understand that the mechanical properties and stability are superior to the conventional one from a comparison of the sintered body with a film type of humidity sensor, because of the high temperature needed in manufacturing and a very large surface area formed by many small particles and grains at the inner part of the sintered body. However, it should be noted that the humidity sensor of the compositions stated before and after is not limited to the case of the sintered body, and that ordinary and well known structures for a humidity sensor including a film on an insulating substrate are also available for the composition of the present invention.

EXAMPLE 2

Figure 2:
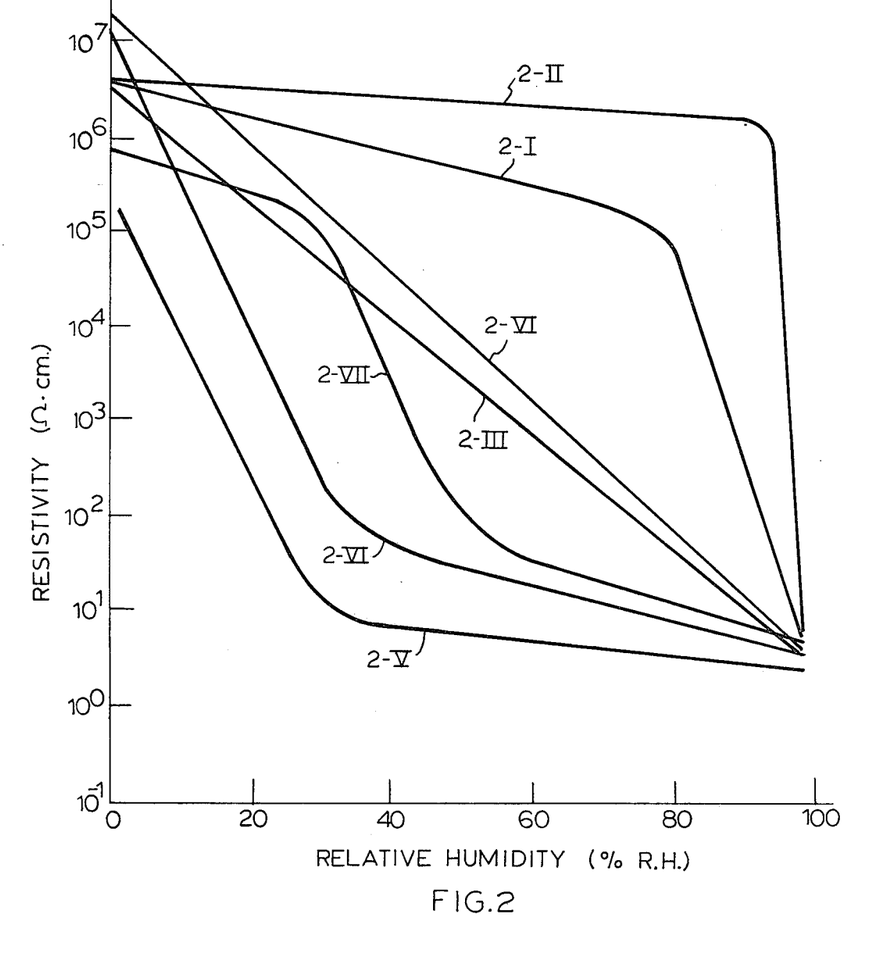

A starting composition as listed in Table 2 was sintered at temperatures as listed in Table 2, and the humidity sensors were prepared. The humidity-resistivity characteristics of the resultant sensors were measured in the same manner as in Example 1. The results of the measured humidity-resistivity characteristics are shown in FIG. 2. As shown in FIG. 2, the sintering temperature in this invention is limited to a temperature between 800° to 1400° C, because a temperature lower than 800° C fails to provide a stable sintered body for the humidity sensor and a temperature higher than 1400° C results in over-sintered body and no humidity sensitive resistor.

EXAMPLE 3

Figure 3:
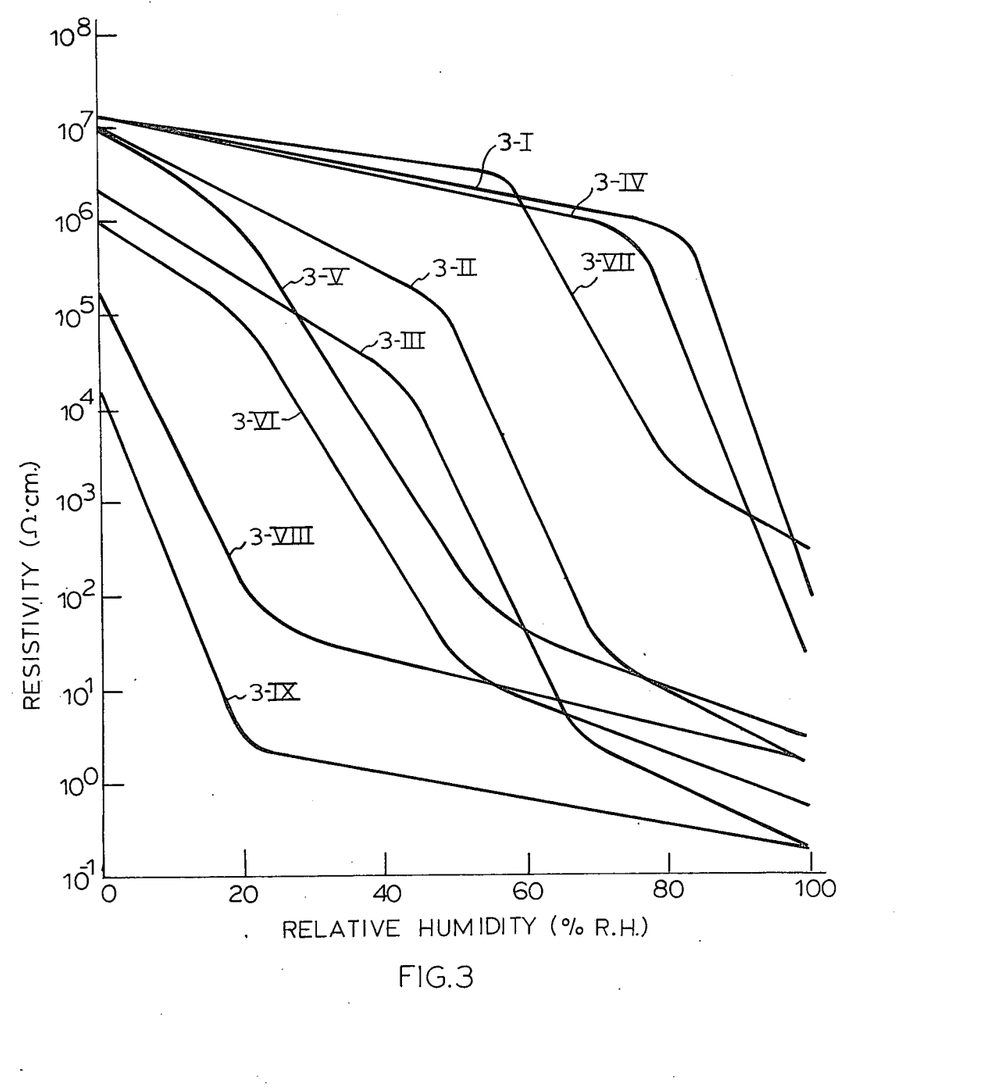

A starting composition as listed in Table 3 was sintered at 1300° C for 2 hours, and the humidity sensors were prepared. The humidity-resistivity characteristics of the resultant sensors were measured in the same manner as that of Example 1. The results of the measurement are shown in FIG. 3. As shown in FIG. 3, the humidity-resistivity characteristics of the resultant humidity sensors changed according to kind and amount of the used alkali metal oxide. That is, an exponentially functional relationship between the relative humidity and the resistivity is found in the region of medium humidity, high humidity or dry state (low humidity) according to the alkali metal oxide used. For the same amount of alkali metal oxide, it is understood from FIGS. 1 and 3 that the humidity range showing abrupt change in resistivity with an exponentially functional relationship shifts from high humidity range to low humidity range in the order lithium oxide, sodium oxide, potassium oxide and cesium oxide. For example, for 10 mole percent of alkali metal oxide, this is shown by the curves in the order of 3-II, 3-V, 1-VI and 3-VIII in FIGS. 3 and 1.

EXAMPLE 4

Figure 4:
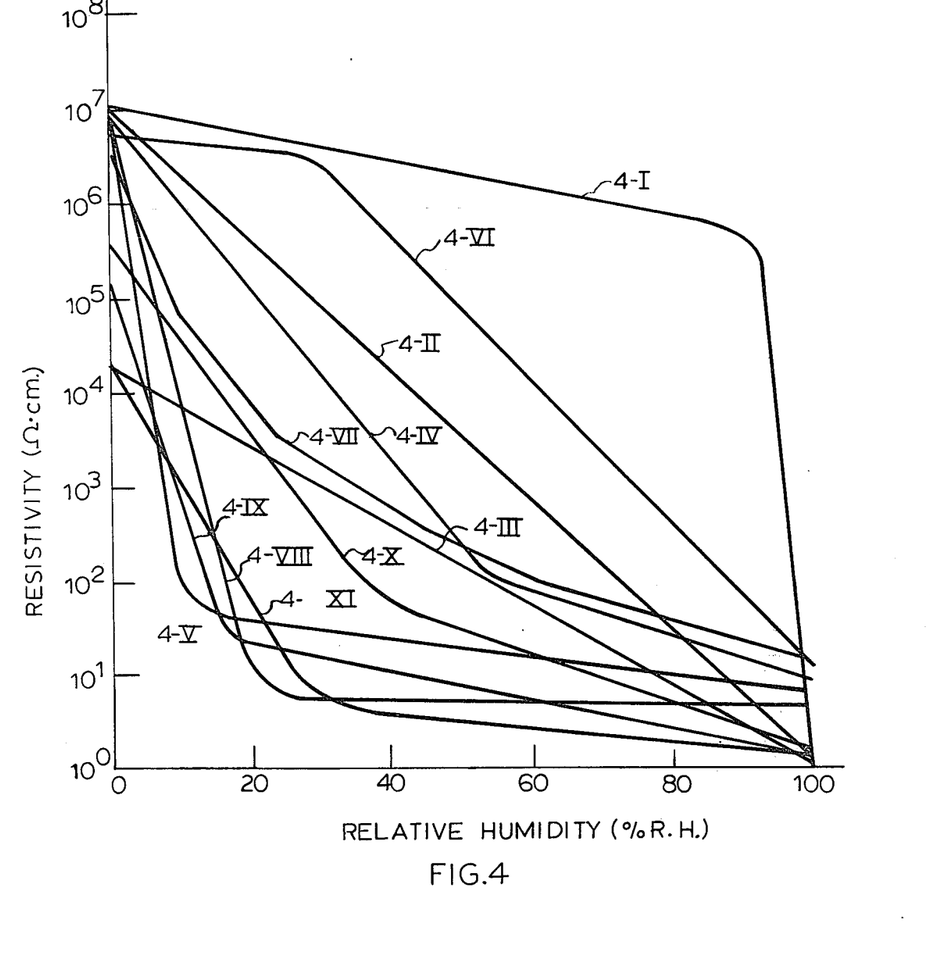

As an additive, more than two alkali metal oxides as listed in Table 4 were mixed with iron oxide, and then the mixture was pressed and sintered at 1300° C for 2 hours. The humidity-resistivity characteristics of the resultant humidity sensors were measured in the same manner as that of Example 1. The results of the measurement are shown in FIG. 4. As shown in FIG. 4, the humidity-resistivity characteristics of the resultant humidity sensors are changed according to kind and amount of the more than two alkali metal oxides employed. That is, an exponentially functional relationship between the relative humidity and the resistivity is found in the region of medium humidity, high humidity, low humidity or the whole humidity according to the combination and the amount of alkali metal oxides.

EXAMPLE 5

The humidity sensors provided in the above examples were placed in a constant humidity and temperature chamber, and temperature dependence of the humidity-resistivity characteristics was measured at a temperature from 0° to 100° C. The results are shown in Table 5, in which the temperature dependence of the humidity-resistivity characteristics is shown in temperature dependence of humidity (the read out humidity change caused by resistivity change). Table 5 also shows the change rates of the samples of Examples 1 and 2 ($K_2O$), Example 3 ($Li_2O$, $Na_2O$ or $Cs_2O$) and Example 4 (more than two of these alkali metal oxides) after various tests, respectively. In the temperature test the sensor was held at 200° C for $5 \times 10^3$ hours at the usual room humidity (about 5% R.H.) with 10V peak to peak AC load. After the temperature test, the humidity-resistivity characteristics of the sensor were measured, and the deviation thereof from the initial ones is shown in Table 5 as the change rate after test in %R.H. Similarly, the humidity test was performed at 80° C in 70 %R.H. for $5 \times 10^3$ hours with 10V peak to peak AC load. The humidity cycle test was carried out by imposing $10^4$ cycles of humidity between 5 and 90 %R.H. at 80° C to the samples while keeping them at each humidity for 15 minutes with 10V peak to peak AC load. The heat shock test was carried out by imposing $10^2$ times of heat shock of $-40°$ and 150° C to the samples while keeping them at each temperature for 30 minutes. The stored lift test involved storing the samples on a shelf with or without an AC load of 10V peak to peak for 1 year at normal temperature, atmospheric pressure and humidity, i.e., 2° to 30° C, around 1 atm. and 40 to 80 %R.H., respectively. Similarly to the case of temperature dependence, all the change rates of the humidity-resistivity characteristics in Table 5 are shown in change rate of humidity. From Table 5, it is clear that all the change rates are very small and so the sensor of the invention can be used practically without problems. Even after gas test and scribing test, there was not observed any appreciable changes in resistivity-humidity characteristics of the humidity sensor.

EXAMPLE 6

Figure 6:
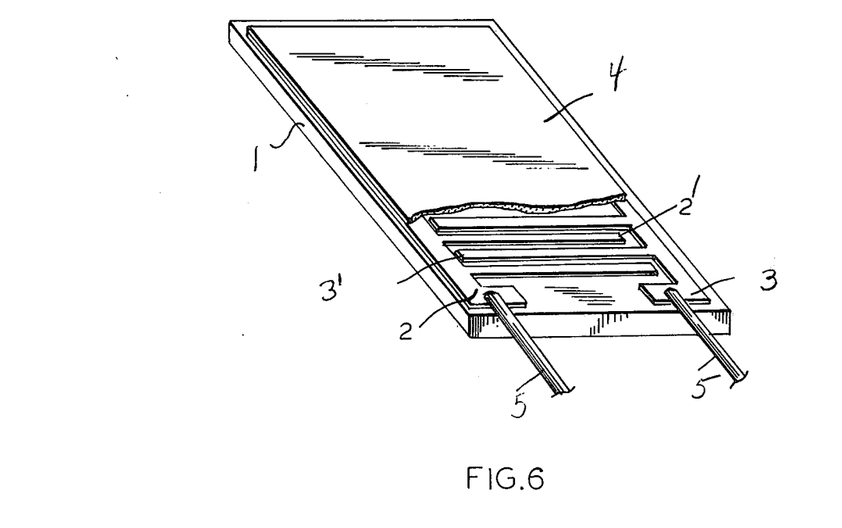
FIG. 6 is a perspective, partially broken out, view of another embodiment of the humidity sensor of the invention.
Figure 7:
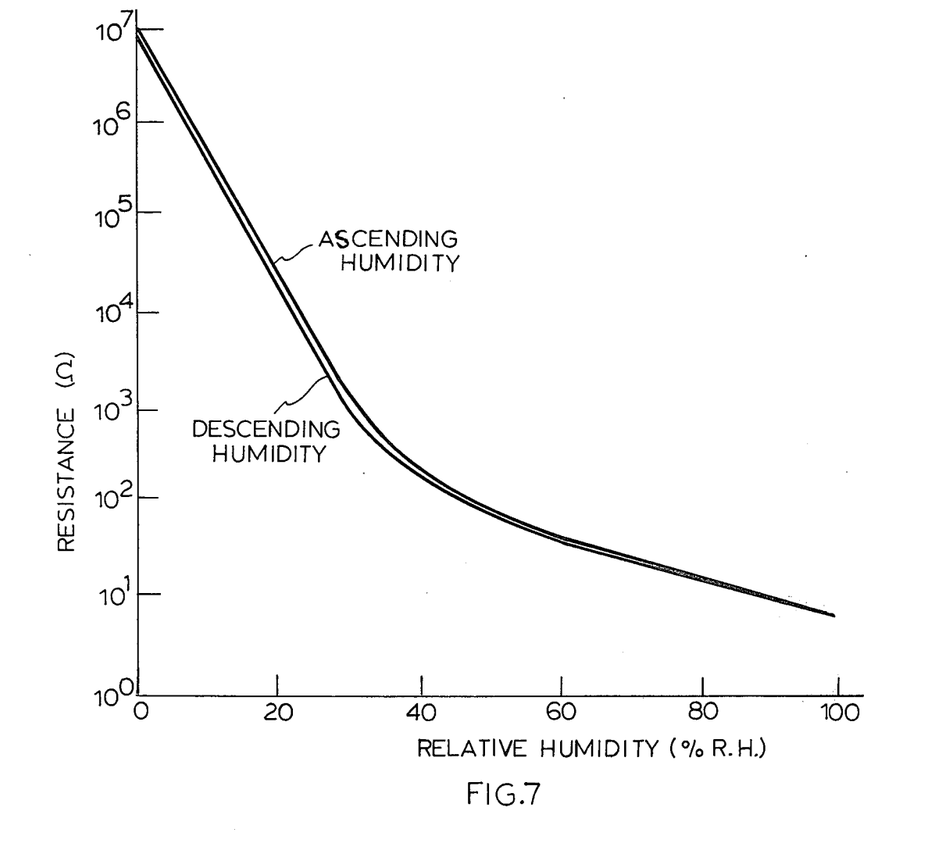
FIG. 7 is a graph showing the hysteresis characteristics of the humidity sensor of the invention.

By using the representative composition of No. 1-VI in Example 1 according to the invention, a surface type humidity sensor was made as follows. The disc of the sintered body having a composition of 90 mole percent of iron oxide and 10 mole percent of potassium oxide obtained in the same manner as that of Example 1 was crushed with a wet mill to obtain fine particles of less than 1 micron in mean diameter. The crushed powder was mixed with 5 wt. percent of ethyl cellulose solution and 0.8 wt. percent of tannic acid. The mixture was kneaded for 1 hour by a kneader to prepare a paste. The thus obtained paste was applied by screen painting to a substrate 1 of aluminum oxide porcelain shown in FIG. 6, which was 10 × 20 mm and 1 mm in thickness, and on which gold electrodes 2 and 3 of about 50 microns thick were applied with eight and nine comblike projections 2' and 3' having widths of 0.2 mm, respectively. The projections 2' and 3' were spaced 0.3 mm apart. The film was painted on the substrate in an approximately 10 mm width covering the comblike electrodes 2' and 3' and was dried at 100° C for about 30 minutes and then was fired in air at 1000° C for 2 hours to form a semiconducting film 4. Then copper wires 5 of 0.8 mm in diameter were attached to the gold electrodes 2 and 3, and there was obtained a surface type humidity sensing resistive element. The resistivity-humidity characteristics of the resultant resistor were measured in the same manner as that of Example 1, and the results are shown in FIG. 7, it is observed that hysteresis of the sensor is very small, e.g., ± 2% R.H. at most. That is, the read-out humidity change caused by the change in resistivity between ascending humidity and descending humidity is very small. It is also clear that the resistivity change is very abrupt in low humidity region and the change ratio in resistivity between 0 %R.H. and 50 %R.H. is higher than $10^4$ times. No appreciable change in resistivity-humidity characteristics was observed after several tests under conditions to be encountered expected in practical use for a dry state sensor.

Table 1

| Nos. | Composition (mole %) | |
|---|---|---|
| | Fe$_2$O$_3$ | K$_2$O |
| 1-I | 99.99 | 0.01 |
| 1-II | 99 | 1 |
| 1-III | 98 | 2 |
| 1-IV | 97 | 3 |
| 1-V | 95 | 5 |
| 1-VI | 90 | 10 |
| 1-VII | 75 | 25 |
| 1-VIII | 10 | 90 |

Table 2

| Nos. | Composition (mole %) | | Sintering Condition | |
|---|---|---|---|---|
| | Fe$_2$O$_3$ | K$_2$O | °C | Hrs. |
| 2-I | 99.99 | 0.01 | 800 | 50 |
| 2-II | 99.99 | 0.01 | 1400 | 2 |
| 2-III | 98 | 2.0 | 900 | 10 |
| 2-IV | 98 | 2.0 | 1350 | 0.5 |
| 2-V | 90 | 10 | 850 | 30 |
| 2-VI | 90 | 10 | 1200 | 2 |
| 2-VII | 90 | 10 | 1400 | 5 |

Table 3

| Nos. | Composition (mole %) | | |
|---|---|---|---|
| | Fe$_2$O$_3$ | Alkali metal oxide | |
| 3-I | 99.99 | Li$_2$O | 0.01 |
| 3-II | 90 | Li$_2$O | 10 |
| 3-III | 10 | Li$_2$O | 90 |
| 3-IV | 99.99 | Na$_2$O | 0.01 |
| 3-V | 90 | Na$_2$O | 10 |
| 3-VI | 10 | Na$_2$O | 90 |
| 3-VII | 99.99 | Cs$_2$O | 0.01 |
| 3-VIII | 90 | Cs$_2$O | 10 |
| 3-IX | 10 | Cs$_2$O | 90 |

Table 4

| Nos. | Additive (mole %) | | | |
|---|---|---|---|---|
| | Li$_2$O | Na$_2$O | K$_2$O | Cs$_2$O |
| 4-I | 0.005 | — | 0.005 | — |
| 4-II | 5 | — | 5 | — |
| 4-III | 45 | — | 45 | — |
| 4-IV | — | 5 | 10 | — |
| 4-V | — | — | 10 | 5 |
| 4-VI | 10 | 5 | — | — |
| 4-VII | — | 10 | — | 5 |
| 4-VIII | 5 | 0.05 | 10 | — |
| 4-XI | 0.005 | — | 10 | 5 |
| 4-X | — | 5 | 10 | 0.005 |
| 4-XI | 10 | 5 | 10 | 2 |

Table 5

| | Temperature dependence %R.H./°C | Change rate after test (%R.H.) | | | | |
|---|---|---|---|---|---|---|
| | | Temperature Test | Humidity Test | Humidity Cycle | Heat Shock Test | Stored Life Test |
| Example 1 and 2 | −0.7 to −0.5 | +3.3 to 5.6 | −3.5 to 4.8 | +2.0 to 5.1 | +0.1 to 0.3 | −2.0 to +100 |
| Example 3 | −1.0 to −0.8 | +4.9 to 7.2 | −5.0 to 6.2 | +7.2 to 9.8 | +0.3 to 0.5 | −5.0 to −0.2 |
| Example 4 | −0.4 to 0.3 | +3.0 to 5.0 | −2.0 to 4.5 | +1.0 to 4.2 | +0.2 to 0.3 | −2.0 to −0.1 |

What is claimed is:

1. A humidity sensor comprising a sintered material having electrodes applied thereto, said sintered material having a negative coefficient of resistivity for relative humidity and comprising 99.99 to 10 mole percent of iron oxide (Fe$_2$O$_3$) and 0.01 to 90 mole percent of at least one member selected from the group consisting of lithium oxide (Li$_2$O), sodium oxide (Na$_2$O), potassium oxide (K$_2$O) and cesium oxide (Cs$_2$O).

2. A humidity sensor according to claim 1, wherein said member is potassium oxide (K$_2$O).

3. A humidity sensor according to claim 1, wherein said member is present in an amount of 0.01 to 25 mole percent.

4. A humidity sensor according to claim 2, wherein said potassium oxide (K$_2$O) is present in an amount of 0.01 to 25 mole percent.

5. A humidity sensor according to claim 4, wherein said potassium oxide (K$_2$O) is present in an amount of 0.01 to 2.0 mole percent.

6. A humidity sensor according to claim 4, wherein said potassium oxide (K$_2$O) is present in an amount of 2.0 to less than 4.0 mole percent.

7. A humidity sensor according to claim 4, wherein said potassium oxide (K$_2$O) is present in an amount of 4.0 to 25 mole percent.

8. A humidity sensor according to claim 1, wherein said alkali metal, oxide is lithium oxide (Li$_2$O).

9. A humidity sensor according to claim 1, wherein said alkali metal oxide is sodium oxide (Na$_2$O).

10. A humidity sensor according to claim 1, wherein said alkali metal oxide is cesium oxide (Cs$_2$O).

11. A humidity sensor according to claim 1 wherein said sintered material is in the form of a disc or film.

* * * * *